United States Patent [19]

Sauter

[11] 4,157,399
[45] Jun. 5, 1979

[54] BENZO(b)THIOPHENES

[75] Inventor: Fritz Sauter, Vienne, Austria

[73] Assignee: Parcor, Paris, France

[21] Appl. No.: 857,134

[22] Filed: Dec. 5, 1977

[30] Foreign Application Priority Data

Dec. 23, 1976 [AT] Austria .................................. 9587/76
Sep. 12, 1977 [AT] Austria .................................. 6527/77
Jul. 29, 1977 [AT] Austria .................................. 6528/77

[51] Int. Cl.$^2$ ..................... A61K 31/38; C07D 333/66
[52] U.S. Cl. .................................. 424/275; 542/422;
424/248.51; 424/250; 424/267; 424/274;
544/146; 544/376; 546/202; 546/226;
260/326.84; 260/330.5
[58] Field of Search ........... 260/330.5, 326.84, 293.57;
544/146, 376; 424/248.51, 250, 267, 274, 275

[56] References Cited

U.S. PATENT DOCUMENTS 3,897,427  7/1975  Sauter .................................. 544/166

OTHER PUBLICATIONS

Chippendale et al., J. Chem. Soc.-Perkin Transactions I, (1972), No. 16, pp. 2023–2030.

Primary Examiner—John M. Ford
Assistant Examiner—Bernard Dentz

[57] ABSTRACT

The present invention relates to new derivatives of 2-phenyl -benzo(b)thiophene mono- or disubstituted on the nitrogen atom of formula

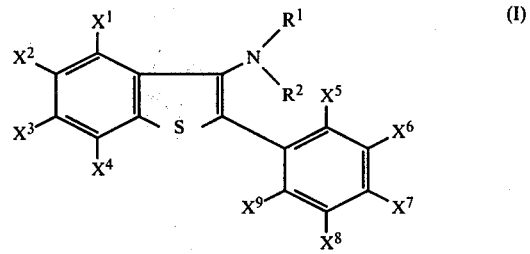

in which $X^1$ to $X^9$ which are identical or different are hydrogen, alkyl having up to 3 carbon atoms, chlorine, bromine, methoxy or methylthio, $R^1$ is hydrogen, alkyl having up to 8 carbon atoms, optionally chlorinated or methoxylated, phenyl optionally chlorinated or methoxylated, aralkyl having in all up to 9 carbon atoms, optionally chlorinated or methoxylated on the phenyl nucleus, $R^2$ is hydrogen, phenyl, or a radical of the formula

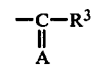

in which
A is two hydrogen atoms or one oxygen atom and
$R^3$ can assume the same meanings as given for $R^1$, the meanings assumed by $R^1$ and $R^3$ being independent from one another, or $R^1$ and $R^2$ together form the radical of a Schiff base of formula

=CH—R$^4$        (III)

in which $R^4$ is not hydrogen, but can otherwise assume the same meanings as $R^3$, or the group

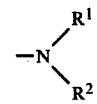

forms the radical of a heterocyclic secondary amine. The invention also relates to the acid addition salts of the above compounds, notably those which are pharmaceutically compatible. The compounds of formula I are useful in normalizing the blood lipid value.

7 Claims, No Drawings

BENZO(b)THIOPHENES

The present invention relates to new derivatives of 2-phenyl-benzo(b)thiophene mono- or disubstituted on the nitrogen atom of formula

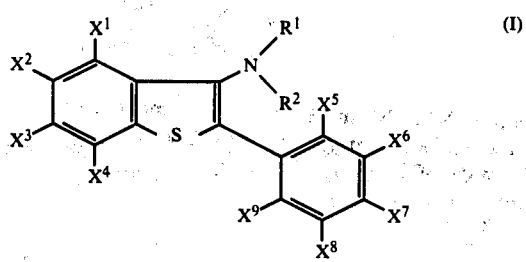

(I)

in which $X^1$ to $X^9$ which are identical or different are hydrogen, alkyl having up to 3 carbon atoms, chlorine, bromine, methoxy or methylthio, $R^1$ is hydrogen, alkyl having up to 8 carbon atoms, optionally chlorinated or methoxylated, phenyl optionally chlorinated or methoxylated, aralkyl having in all up to 9 carbon atoms, optionally chlorinated or methoxylated on the phenyl nucleus, $R^2$ is hydrogen, phenyl, benzyl or a radical of formula:

(II)

in which A is two hydrogen atoms or one oxygen atom and $R^3$ can assume the same meanings as given for $R^1$, the meanings assumed by $R^1$ and $R^3$ being independent from one another, or $R^1$ and $R^2$ together form the radical of a Schiff base of formula:

$$=CH-R^4$$ (III)

in which $R^4$ is not hydrogen, but can otherwise assume the same meanings as $R^3$, or the group

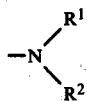

forms the radical of a heterocyclic secondary amine which, in the case of piperazine, can, as appropriate, be substituted on the second nitrogen atom by an alkyl having up to 6 carbon atoms, by an aliphatic or aromatic acyl having up to 8 carbon atoms, by a phenyl optionally chlorinated or methoxylated or by an aralkyl optionally chlorinated or methoxylated on the phenyl nucleus, having in all up to 9 carbon atoms.

The invention also relates to the acid addition salts of the above compounds, notably those which are pharmaceutically compatible.

Preferred compounds are those in which $X^1$, $X^3$, $X^8$ and $X^9$ are hydrogen and $R^2$ is alkyl, aryl or aralkyl. Particularly preferred are N,N-dialkylated derivatives and 2-phenyl benzo(b)thiophenes substituted in 3 position by nitrogenous heterocycles and having or not having the benzene nucleus of benzothiophene or the phenyl nucleus at the 2 position monochlorinated or monomethoxylated.

Notably preferred are compounds of formula:

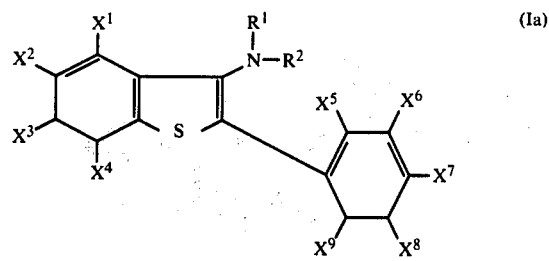

(Ia)

and, more particularly, those in which $X^1$ is not hydrogen when $X^4$ is not hydrogen. The radicals $R^1$ and $R^2$ preferably form, together with the nitrogen atom to which they are attached, the radical of a heterocyclic secondary amine which, in the case of piperazine, can be optionally substituted on the second nitrogen atom by an aralkyl radical having up to 9 carbon atoms at most in all and whose phenyl nucleus can be alkylated, chlorinated or methoxylated by radicals having up to 6 carbon atoms at most.

Compounds of formula:

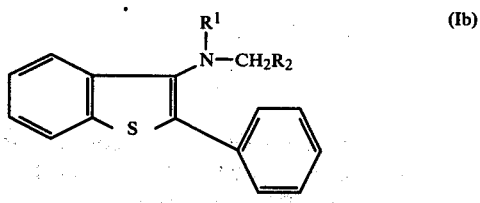

(Ib)

in which $R^1$ is alkyl having up to 4 carbon atoms or benzyl and $R^2$, independently of $R^1$, is hydrogen, alkyl having up to 3 carbon atoms or phenyl are likewise of great interest.

Compounds of formula

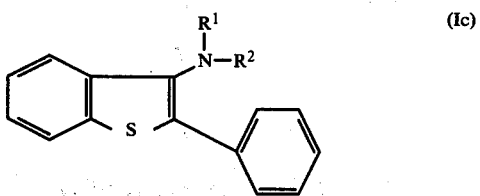

(Ic)

in which $R^1$ is alkyl having up to 4 carbon atoms, phenyl or benzyl and $R^2$, independently of $R^1$, is alkyl having up to 4 carbon atoms or benzyl are endowed with particularly interesting properties.

The novel compounds of formula I are intermediate products valuable for the synthesis of novel medicines. They also possess in themselves remarkable properties for normalising the blood lipid level. This is particularly true of the first-mentioned class of preferred compounds which, either alone or mixed with other active substances in the form of conventional galenic preparations, are surprising hypocholesterolemiants and hypolipemiants, while having low toxicity.

The object of the invention is also a process for the preparation of compounds of formula I consisting of:

(a) reacting 2-phenyl-thioindoxylic derivatives of formula:

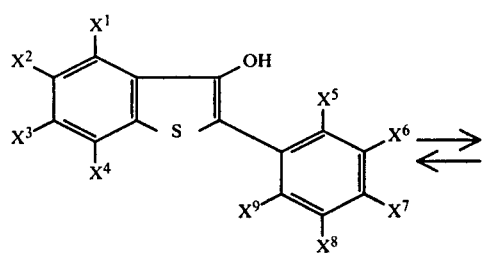

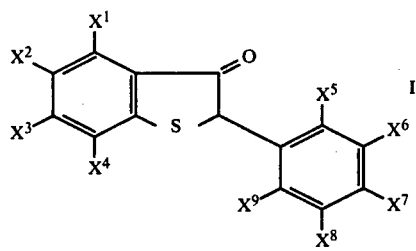

in which $X^1$ to $X^9$ have the aforementioned meaning with compounds of formula:

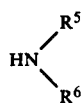  (V)

in which $R^5$ and $R^6$ do not together represent the radical of a Schiff base, but otherwise $R^5$ corresponds to $R^1$ and $R^6$ corresponds to $R^2$ or the group

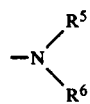

has the same meaning as the group

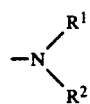

with elimination of water, appropriately with the addition of simple carboxylic acid and/or catalyst such as Lewis acids, to obtain compounds of formula I in which $R^1$ and $R^2$ or the group

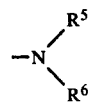

have the meanings of $R^5$ and $R^6$ or of

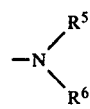

of formula V, or
  (b) acylating or alkylating in a conventional manner primary or secondary amines of formula:

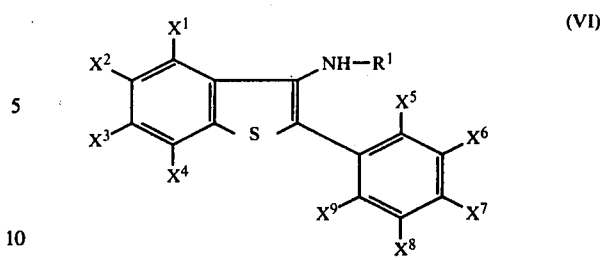

in which $X^1$ to $X^9$ and $R^1$ have the same meaning as in formula I, for example by means of alkylating or acylating agents of formula:

$$R^2\text{—}Z \qquad (VII)$$

in which $R^2$ has the same meaning as in formula I and Z is a labile group allowing nucleophilic exchange, to obtain compounds of formula I in which $R^1$ and $R^2$ do not together represent the radical of a Schiff base and the group

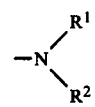

does not represent the radical of a heterocyclic secondary amine, but otherwise $R^1$ and $R^2$ have the same meaning as indicated for formula I, or
  (c) converting compounds acylated at the nitrogen of formula:

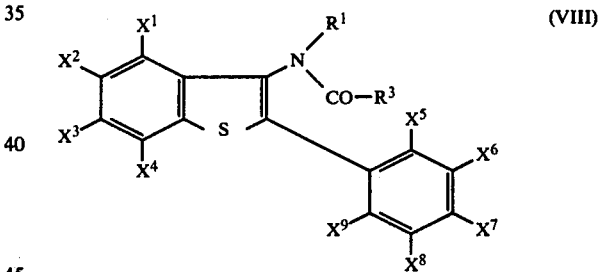

in which $X^1$ to $X^9$ and $R^1$ have the same meaning as in formula I and $R^3$ has the same meaning as in formula II, either by hydrolysis to obtain the compounds of formula VI or by reduction with $LiAlH_4$ to obtain compounds of formula:

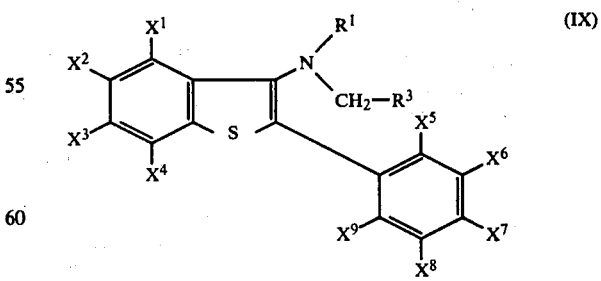

in which $X^1$ to $X^9$, $R^1$ and $R^3$ have the same meanings as in formula VIII, or
  (d) forming, from primary or secondary amines of formula VI by the action of $NaBH_4$ and carboxylic acids of formula:

R$^3$—COOH  (X)

in which R$^3$ has the same meaning as in formula II, either, where R$^1$ is not hydrogen, compounds of formula IX in which R$^1$ is not hydrogen, or, where R$^1$ is hydrogen, preferably compounds of formula:

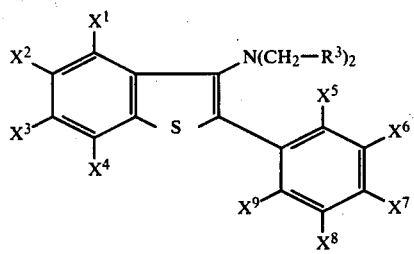
(XI)

in which X$^1$ to X$^9$ and R$^3$ have the same meanings as in formula VIII, or (e) reacting compounds of formula:

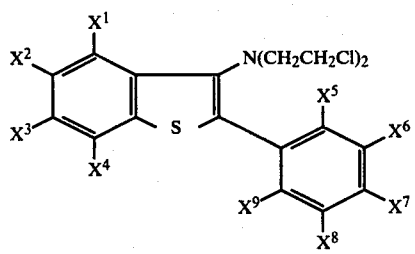
(XII)

in which X$^1$ to X$^9$ have the same meanings as in formula I with primary amines of formula:

R$^7$—NH$_2$  (XIII)

in which R$^7$ is hydrogen, simple alkyl having up to 6 carbon atoms, phenyl optionally chlorinated or methoxylated or aralkyl having at most 9 carbon atoms in all and optionally chlorinated or methoxylated on the phenyl nucleus, to form compounds of formula:

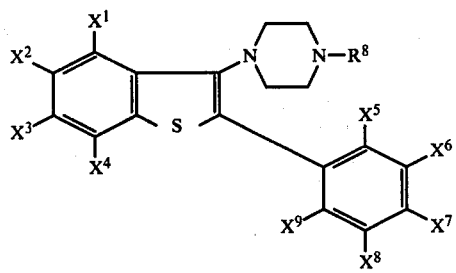
(XIV)

in which X$^1$ to X$^9$ have the same meanings as in formula I and R$^8$ has the same meaning as R$^7$ in formula XIII, or (f) converting compounds of formula XIV in which R$^8$ is the benzyl radical, by debenzylation, into compounds of formula XIV for which R$^8$=H, which, in turn, by the appropriate action of conventional acylating, alkylating or aralkylating agents, are converted into compounds of formula XIV in which R$^8$ is acyl, alkyl or aralkyl, or (g) reacting primary amines of formula VI in which R$^1$=H with aldehydes of formula:

R$^4$—CHO  (XV)

in which R$^4$ has the same meaning as in formula III, to obtain Schiff bases of formula:

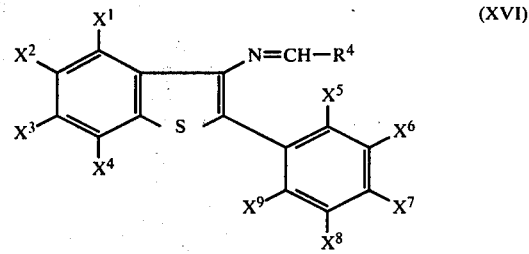
(XVI)

in which X$^1$ to X$^9$ and R$^4$ have the same meanings as in formulas I and III, which, in turn, appropriately by reduction or hydrogenation, notably by the action of complex hydride, particularly NaBH$_4$, can be converted into compounds of formula IX in which R$^1$ is hydrogen and R$^3$ is not simultaneously hydrogen, that is, R$^3$=R$^4$, or (h) converting amides of formula:

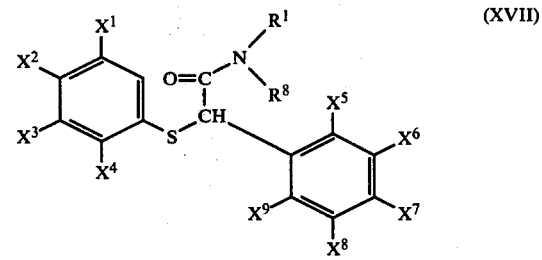
(XVII)

in which R$^1$ and R$^8$ are identical or different and R$^1$ has the same meaning as in formula I, while R$^8$ is not acyl, but otherwise has the same meaning as R$^2$ in formula I, the group

having the same meaning as the group

of of formula I, by the action of a cyclising agent such as P$_2$O$_5$ or polyphosphoric acid, into compounds of formula I or their salts, in which R$^1$ and R$^2$ have the same meaning as R$^1$ and R$^8$ in formula XVII or in which the group

has the meanings indicated in formula I, it being possible optionally to convert the basic compounds obtained into salts by the action of acid in a conventional manner.

To obtain secondary amines of formula I from primary amines of formula VI in which R$^1$=H, the reduction of the corresponding acylated derivatives of formula VIII (alternative c of the process) or of the Schiff bases of formula XVI (alternative g of the process) is preferred, although it is also possible to obtain the same compounds from the same starting substances by direct alkylation or direct aralkylation according to alternative b of the process or by the action of NaBH$_4$ and corresponding carboxylic acids (alternative d of the process), although with lower yields. It is likewise often better, when preparing unsymmetrical dialkyl compounds, to apply the action of carboxylic acids and NaBH$_4$ rather than resort to the other possible alternatives, whereas when preparing symmetrical dialkyl products, for example, N'-alkyl-piperazinyl products it is better to resort to alternative h of the process.

The various alternatives are explained further hereinafter.

The reaction according to alternative a of substituted 2-phenyl-thioindoxyl with the compounds of formula V is particularly suitable for obtaining secondary amines and amides of formula I.

The reaction of compounds of formula IV with primary amines enables otherwise rather long reaction periods to be shortened at tempratures over 100° and more often between 120° and 200°, preferably between 140° and 200°. To this end, work can be carried out in a solvent inert to bases with a high boiling point, preferably using an excess of base as solvent. If bases with a low boiling point are used, it is recommended to work at pressure in an autoclave which is adjusted according to the reaction temperature between 140° and 200°. The excess primary amine involved can be collected at the end of the reaction by distillation.

The secondary amines thus obtained can be purified by washing the base (optionally dissolved in methylene chloride) with dilute HCl and, in practice, only the primary amine used as starting substance is eliminated in the form of an aqueous saline solution. By washing with dilute aqueous alkali the unchanged thioindoxylic constituent is eliminated. In the case of bases crystalling slowly, the crude products can be purified by means of hydrochlorides which can be obtained by the action of hydrochloric gas on the solution of the secondary amine in an inert solvent such as chloroform.

Analogous reactions with (optionally heterocyclic) secondary amines require, to obtain useful yields, definitely longer reaction periods, for example, heating for one day at temperatures between 140° and 200°. It is recommended to use an excess of base. The addition of Lewis acid, for example, AlCl$_3$+ZnCl$_2$ as catalyst, definitely increases the yield.

Analogous reactions with amides, preferably N-formylated compounds of formula R$^1$-NH-CHO(R$^1$ having the same meaning as in formula I.

These reactions are preferably carried out with an excess of the amide used as starting material at reaction temperatures between 150° and 200° C., for example, at a bath temperature of approximately 190° C. It is recommended to involve an excess of approximately 1 to 5 moles of the acid corresponding to the acyl radical (thus, for example, HCOOH for formyl compounds), because very pure acylated products can be obtained in this way.

When hydrolysis is to follow the formation of acylated products, it is often sufficient to wash the crude product throughly in water to purify it. However, before a subsequent reduction stage it is advisable to recrystallise the dried crude product in an inert solvent, for example, benzene, chloroform or an acetate.

Direct substitution on nitrogen according to alternative b of the process which leads to compounds that could be prepared, for example, by alternative a of the process is particularly appropriate for the manufacture of mono-acylated derivatives and, for example, compounds of formula I which are substituted on the nitrogen in the same way. As examples of alkylating agents of formula VII mention may be made, notably, of alkyl chlorides, bromides or iodides and aralkyl chlorides, bromides or iodides, optionally substituted, as well as sulphates and the corresponding tosylates and allied reagents.

To prepare N,N-dimethylated compounds of formula I from NH$_2$ compounds, it is possible to methylate by means of methyl halide and, more particularly, by means of dimethyl sulphate or by means of CH$_2$O+HCOOH by the Eschweiler-Clarke method, the reaction conditions being the conventional ones for such reactions.

Acylation is carried out conventionally by reaction e.g. with acyl halides or with anhydrides.

The reduction, notably with LiAlH$_4$, of the acylated compounds of formula VIII according to alternative c of the process represents a favourable way of synthesising compounds of formula I monosubstituted on nitrogen or disubstituted on nitrogen in a different manner. This reduction is carried out conventionally by using as solvent an ether with a high boiling point, preferably dioxan, working at temperatures of 60° C. for 10 minutes to 4 hours and preferably for 20 to 90 minutes, with an excess of LiAlH$_4$ of 1 to 2 equivalents, so as to obtain good yields. The final products can be purified via the corresponding salts, notably the hydrochlorides prepared in anhydrous solvents. The acylated compounds can be hydrolysed by acid or alkali, for example, by heating from 2 to 10 hours, preferably from 4 to 8 hours, with hydrochloric acid at 15 to 25% at reflux temperature, stirring being useful because of the heterogeneity of the reaction mixture. It is recommended to follow the reaction with thin—layer chromatography, since the optimum reaction period largely depends on the substituents on the nitrogen and as excessively long hydrolysis periods can cause partial decomposition of the product formed.

Alternative d of the process is particularly useful for preparing tertiary amines of formula I, although they can also be used to prepare secondary amines. Often, for example, when preparing compounds of formula I in which R$^1$ and R$^2$ are lower alkyl with the exception of methyl, this alternative is preferable to direct alkylation by alkyl halides. This alternative is particularly suitable for obtaining compounds of formula I in which R$^1$ and R$^2$ are halogenated substituents, as is the case, for example, in the compounds of formula XII.

If liquid carboxylic acids are used, a solution is prepared of the primary or secondary amine of formula VI to be alkylated in an inert anhydrous solvent such as benzene or tetrahydrofuran, and then NaBH$_4$ is added and the carboxylic acid is poured dropwise with cooling.

If it is intended to obtain double alkylation of the primary amines, it is recomended, to obtain good yields, to use a large excess of NaBH$_4$ and carboxylic acid, notably at least three times the molar quantity of carboxylic acid in relation to NaBH$_4$. When the addition of the carboxylic acid is completed, the mixture is heated for 10 to 60 minutes, preferably between 50° and 120° C. If solid carboxylic acids are used, it has proved favourable to dissolve them in an inert solvent, then add NaBH₄ with cooling, and then, after the addition of the amine, heat as indicated above.

Alternative e of the process according to the invention represents one of the possibilities for preparing piperazine derivatives of formula XIV. Reaction of a compound of formula XII with those of formula XIII can be carried out with or without a solvent (such as diphenyl ether or tetrahydrofuran) and with the addition of a basic agent such as $K_2CO_3$ or an excess of $R^7$—$NH_2$ to bind HCl. It is advisable to apply reaction temperatures between 100° and 160° C., and to use autoclaves, if necessary, with reaction periods of 3 hours to 5 days (depending on the temperature value), to obtain good yields.

Alternative f of the process enables piperazine derivatives of formula XIV to be obtained, in which $R^8$ is very diverse, by debenzylating compounds benzylated on the nitrogen to give the corresponding NH compounds which can then be resubstituted by a conventional process.

Debenzylation can be carried out by heating for 1 to 10 hours with excess chloroformates, for example, $Cl.COOC_2H_5$, optionally in an inert solvent such as benzene, thus obtaining roughly quantitative yields of urethane. Subsequent hydrolysis to obtain piperazines unsubstituted on nitrogen can be carried out by acid or alkali, for example, by heating with an aqueous alkali and adding alcohols as agents assisting dissolution.

Alternative g of the process enables secondary amines of formula I to be obtained, in which the 3 position of the benzo (b) thiophene carries the group —NH—$CH_2$—$R^4$, and, particularly, compounds in which $R^4$ is a long-chained aliphatic radical or an aromatic radical. They are prepared via the Schiff bases of formula VII which are then reduced, for example, by means of NaBH₄ into the desired compounds. The Schiff bases are obtained conventionally by reacting the corresponding $NH_2$ compounds with aldehydes which are appropriately used in a slight excess. For aldehydes with a high boiling point it is recommended to use a water trap when a suitable solvent such as benzene or toluene is employed.

Alternative h of the process according to the invention enables amines of formula I not acylated on the nitrogen to be prepared favourably. Often, this alternative is preferable, to obtain such compounds, to the majority of other possibilities, for example, to direct alkylation of the $NH_2$ product with alkyl halides, for reasons of yield, or to processes employing acids and NaBH₄, for reasons of economy.

This alternative may be carried out without a solvent, but preferably with an inert solvent, notably chlorobenzene or toluene, by heating in the presence of an appropriate condensation agent, for example, $P_2O_5$, polyphosphoric acid, etc., and, when the tertiary amine is prepared, preferably in the presence of $POCl_3$ which is advantageously used to excess. The reaction periods are between 2 and 20 hours, preferably between 4 and 10 hours, for temperatures between 80° and 160° C. At lower reaction temperatures it is advisable consequently to lengthen the reaction periods.

The starting substances are all easily accessible. 2-phenyl-thioindoxyl and its corresponding derivatives of formula IV can be prepared by the process of L. Kalb and J. Bayer, Ber. dtsch. chem, Ges. 46, 3879 (1913) or by an analogous process or by using the process, conventional in chemistry, of the thioindoxyls of e.g. W. Eckert and O. Bayer in Houben-Weyl, Methoden der organischen Chemie, volume VII/4, 40.

The starting materials of formula XVII are accessible via the carboxylic acids prepared according to the process described by K. Fuchs, Mh. Chem. 53+54, 438 (1929), or Z. J. Vejdelek, O. Nemecek and A. Simek, Coll. Czech. Chem. Commun. 28, 2618 (1963), or by an analogous process, it being possible to convert the carboxylic acids conventionally into amides of formula XVII.

The starting materials of formula I in which $R_1=R_2=H$ can be prepared by reduction of the corresponding 3-nitro compounds, but preferably by hydrolysis of the corresponding N-formylated compounds.

Alternative h applies particularly to the cyclisation of compounds IIa

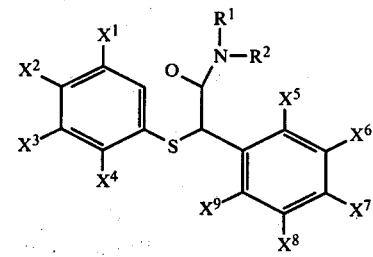

in which $X^1$ to $X^9$, $R^1$ and $R^2$ have the same meaning as in formula Ia.

The amides of the phenylthio-α-phenylacetic acid needed as starting product are readily accessible by preparing them, for example, as follows:

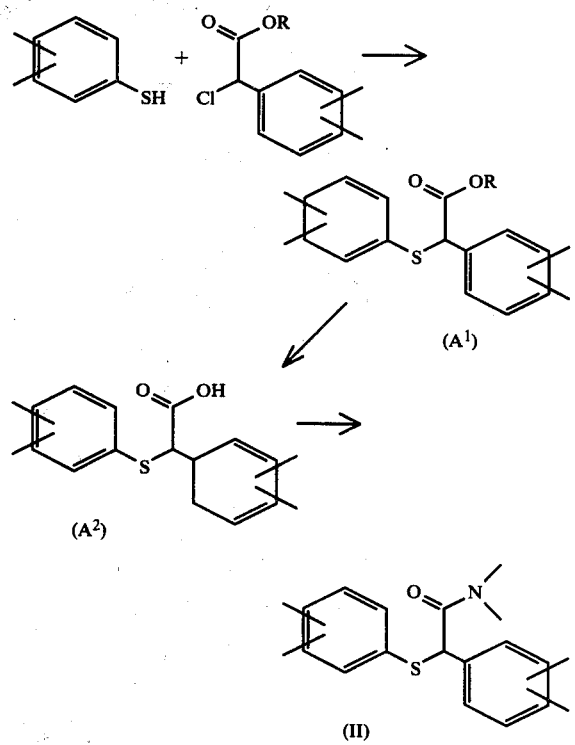

The reaction of optionally substituted thiophenol with optionally substituted, α-chloro-phenyl acetates to obtain esters of formula $A^1$ and the saponification thereof in carboxylic acids of formula $A^2$ can be carried out according to the process described by Z. J. VEJ- DELEK, O. NEMECEK and A. SIMEK, Coll. Czech. Chem. Commun. 28, 2618 (1963) or by an analogous process. These carboxylic acids are converted conventionally into corresponding amides of formula II, for example, by the process described by T. C. ASTHANA and Coll., Indian J. Chem. 8, 1086 (1970), or by an analogous process.

Some amides of formula IIa whose physical characteristics are given hereinafter are novel compounds.

To obtain the compounds of formula Ib:

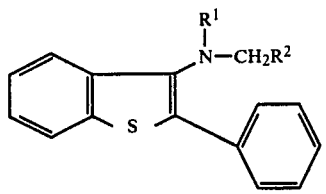
(Ib)

it is possible to alkylate the amines of formula:

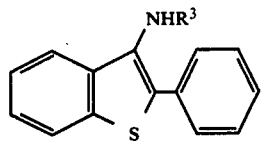
(IIb)

in which $R^3$ is hydrogen, alkyl having up to 4 carbon atoms or benzyl by the simultaneous action of sodium borohydride (NaBH$_4$) and carboxylic acids of formula:

$$R^2COOH \qquad (IIIb)$$

in which $R^2$ has the same meaning as in formula Ib.

Where $R^3$ is hydrogen, that is, when 3-amino-2-phenylbenzo(b)-thiophene is used as starting product, symmetrically substituted tertiary amines are formed in which the substituent $R^1$ is identical to the group $R^2CH_2-$, $R^2$ having the same meaning as in formula IIIb. If, however, secondary amines of formula IIb are used, that is, those in which $R^3$ is not hydrogen, amines of formula Ib are created in which $R^1$ has the same meaning as $R^3$ in formula IIb and $R^2$ has the same meaning as in formula IIIb.

The starting materials needed for this alternative are readily accessible. The primary amine of formula IIb, 3-amino-2-phenyl-benzo(b)thiophene, can be prepared either by reduction of the corresponding nitrated compounds (A$^1$) according to K. E. CHIPPENDALE, B. IDDON and H. SUSCHITZKY, J. Chem. Soc., Perkin Trans. I 1972, 2023, or preferably by reacting 2-phenyl-benzo(b)thiophen-3-ol with formamide and formic acid to obtain the amide (A$^2$), followed by hydrolysis or by condensation of 2-chloro-benzonitrile with benzyl mercaptan. The secondary amines of formula IIb are prepared preferably by indirect alkylation of the primary amine, for example, by acylation into the amide A$^3$ and by subsequent reduction, for example, by means of LiAlH$_4$, or by synthesis or Schiff base A$^4$ and reduction thereof, notably by NaBH$_4$.

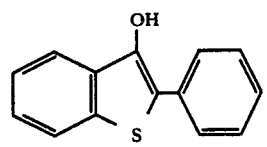
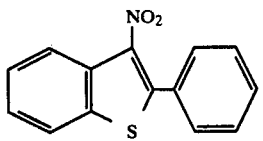
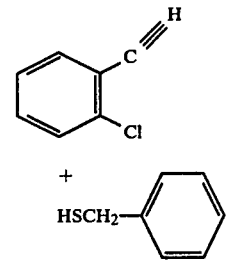
(A$^1$)

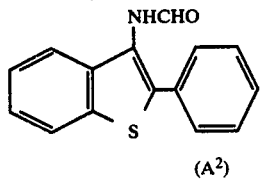
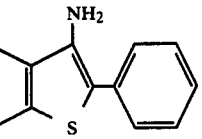
(A$^2$)

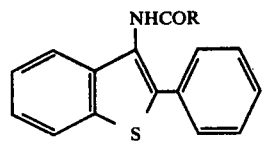
(A$^3$)

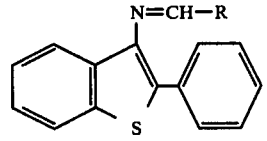
(A$^4$)

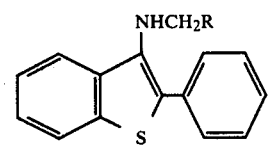

To prepare the compounds of formula Ic it is possible to alkylate starting substances of formula:

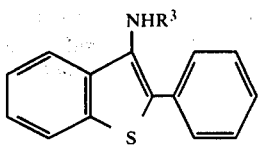

in which $R^3$ is hydrogen, alkyl having up to 4 carbon atoms, phenyl or benzyl, preferably by means of agents of formula:

$$R^2-Z \qquad (IIIc)$$

in which $R^2$ has the same meaning as in formula Ic and in which Z is a labile group suitable for a nucleophilic exchange. To prepare the N,N-dimethylated product, they can be reacted with formalin and formic acid. Typical examples of alkylating agents of formula IIIc are dialkyl sulphates, notably dimethyl sulphate, alkyl tosylates, benzyl tosylate, as well as alkyl chlorides, bromides or iodides or benzyl chloride, bromide or iodide.

Where $R^3$ is hydrogen, that is, when 3-amino-phenyl-benzo(b)thiophene is used as starting substance, symmetrically substituted tertiary amines of formula Ic are formed, in which both $R^1$ and $R^2$ have the same meaning as $R^2$ in the agent of formula IIIc which is employed. However, if secondary amines of formula IIc are applied, that is, those in which $R^3$ is not hydrogen, compounds of formula Ic are created in which $R^1$ has the same meaning as $R^3$ in the secondary amine of formula II employed and $R^2$ has the same meaning as the alkylating agent of formula IIIc which is used.

The bases of formula Ic can form salts by the action of acid giving notably pharmaceutically compatible salts. Because of low basicity of the compounds of formula Ic strong acids are preferably used to this end.

The reaction is carried out by heating the compounds of formula IIc and alkylating agents and the solvent can consist of an excess of the alkylating agent or an inert anhydrous solvent such as acetone, chloroform, benzene or diosan. An acid binding agent such as $K_2CO_3$ is optionally added. If only slightly reactive alkyl chlorides or bromides are used, it is advantageous to allow for the addition of catalysts such as sodium iodide during the reaction. To obtain good yields, there must be reaction periods varying, according to the reactivity of the alkylating agent, between one hour and several days at temperatures from 50° to 200° C., if necessary, using pressure vessels.

Preferred compounds according to the invention are:
2-(4-chloro-phenyl)-3-methylaminobenzo(b)thiophene,
2-phenyl-3-propylamino-benzo(b)thiophene,
3-(4-methoxy-benzylamino)-2-phenylbenzo(b)thiophene,
3-dimethylamino-2-(2'-methoxyphenyl)-benzo(b)thiophene,
3-dimethylamino-5-methyl-2-phenylbenzo(b)thiophene,
7-chloro-3-dimethylamino-2-phenylbenzo(b)thiophene,
5-bromo-2-diethylamino-2-phenylbenzo(b)thiophene,
3-(N-ethyl-N-methylamino)-2-phenylbenzo(b)thiophene 3-diethylamino-2-(4-methylthiophenyl)-benzo(b)thiophene,
5-chloro-2-(4-chlorophenyl)-3-dimethylaminobenzo(b)thiophene,
3-acetamido-2-(4-chlorophenyl)-benzo(b)thiophene,
3-chloroacetamido-2-phenyl-benzo(b)thiophene,
2-(7-chlorophenyl)-3-(piperidino)-benzo(b)thiophene,
2-(5-bromophenyl)-3-morpholino-benzo(b)thiophene,
3-(4-benzoyl piperazino)-2-phenylbenzo(b)thiophene,
3-(4-phenethyl piperazino)-2-phenylbenzo(b)thiophene,
3(-4-ethyl piperazino)-2-phenylbenzo(b)thiophene,
2-(4-chlorophenyl)-5-methoxy-3-(piperadino)-benzo(b)thiophene.

The following examples illustrate the invention.

EXAMPLE 1

3-benzylamino-2-phenyl-benzo(b)thiophene.

A solution of 12.0 g (53 mmol) of 2-phenyl-thioindoxyl is refluxed for 22 hours in 100 milliliters of benzylamine. After the excess benylamine is separated by distillation under reduced pressure, the residue is dissolved in $CH_2Cl_2$ and washed with 2 N HCl. By evaporating the dried organic phase over $Na_2SO_4$ the 3-benzylamino-2-phenyl-benzo(b)thiophene is obtained in the form of a crude oily product. It is dissolved in a little $CHCl_3$ and converted into the hydrochloride by hydrochloric gas: 13.6 g (73% of theory) of yellow crystals in ethanol, decomposition from 170° C. (in a sealed tube).

Preparation of the starting material into a solution of sodium ethoxide prepared from 16.5 g (0.72 gram atom) of sodium and 220 milliliters of absolute ethanol is poured dropwise for 30 minutes with stirring a solution of 117.6 g (0.36 mol) of ethyl α-(2-methoxycarbonylphenylthio)-phenyl acetate in 950 milliliters of absolute ether, and then refluxed with stirring for a further 1 hour. After cooling, it is poured into 2 liters of water and acidified by hydrochloric acid; the organic phase is separated, dried over sodium sulphate and evaporated: 2-phenyl-thioindoxyl, 69.9 g (87% of theory) of colourless needles, the mixture of petroleum ether and benzene melting at 104°–106° C. (decomposition).

EXAMPLE 2

3-hexylamino-2-phenyl-benzo(b)thiophene.

A solution of 8 g (35 mmol) of 2-phenyl thioindoxyl is refluxed for 18 hours in 55 milliliters of standard hexylamine. After the excess hexylamine is separated by distillation under reduced pressure, the residue is dissolved in $CH_2Cl_2$ and 4.0 g of unchanged starting material is recovered by extraction with 2 N NaOH. It is then washed with 2 N HCL. By evaporating the organic phase dried over $Na_2SO_4$, the 3-hexylamino-2-phenyl-benzo(b)thiophene is obtained in the form of a crude oily product. It is dissolved in a little $CHCl_3$ and converted into hydrochloride by hydrochloric gas: 4.2 g (68% of theory related to the 2-phenyl-thioindoxyl which has reacted) of colourless crystals in the mixture of ethanol and ether, decomposition from 142° C. (in sealed tubes).

EXAMPLE 3

3-formamido-2-phenyl-benzo(b)thiophene

A mixture of 60.0 g (0.260 mol) of 2-phenyl-thioindoxyl, 60 milliliters (1.51 mol) of formamide and 16 milliliters of formic acid at 98–100% (0.42 mol) is refluxed with stirring for 24 hours at a bath temperature of 190°. The reaction mixture is then poured, still hot, into water. The still wet precipitated product is triturated, centrifuged and dried: 66.2 g (99% of theory) of 3-formamido-2-phenyl-benzo(b)thiophene; thin colourless needles melting between 185° and 186° C. (benzene).

EXAMPLE 4

3-methylamino-2-phenyl-benzo(b)thiophene.

3.0 g (11.8 mmol) of 3-formamido-2-phenyl-benzo(b)thio-phen and 1.08 g (28.4 mmol) of lithium hydride and aluminium are refluxed with stirring for 30 minutes in 60 milliliters of absolute dioxane. The cooled reaction mixture is mixed with water to decompose the excess lithium and aluminium hydride and, after the addition of approximately 100 milliliters of $CH_2Cl_2$ it is stirred for a further 15 minutes. After centrifuging with the addition of the hyflo, the organic phase is dried over $K_2CO_3$ and evaporated: 3-methylamino-2-phenyl-benzo(b)thiophene in the form of a crude oily product. It is dissolved in a little $CHCl_3$ and converted into the hydrochloride by hydrochloric gas: 2.6 g (80% of theory) of colourless crystals in a mixture of ethanol and ether, decomposition from 198° C. (in sealed tubes).

EXAMPLE 5

3-acetamido-2-phenyl-benzo(b)thiophene.

4.5 milliliters (48 mmol) of acetic anhydride are mixed with a solution of 9.0 g (40 mmol) of 2-phenyl-3-amino-benzo(b)thiophene in 45 milliliters of $CH_2Cl_2$. After attenuation of the exothermic reaction it is left for 2 hours and the precipitated product is centrifuged and washed with ether: 9.6 g (90% of theory) of 3 acetamido-2-phenyl-benzo(b)thiophene, colourless crystals melting between 220° and 221° C. ($CHCl_3$).

Preparation of the starting products:

67.0 g (0.265 mol) of 3-formamido-2-pheny-benzo(b)thiophene and 700 milliliters of HCl at 25% are refluxed with stirring for 8 hours. After cooling, it is diluted with water, neutralised by ammonia and the product is dissolved in $CH_2Cl_2$. By evaporating the organic phase dried over $K_2CO_3$, 58.7 g (98% of theory) of 2-pheny-3-amino-benzo-(b)thiophene are obtained; yellow plates melting between 110° and 112° C. (cyclohexane).

EXAMPLE 6

3-acetamido-2-phenyl-benzo(b)thiophene.

A mixture of 10.0 g (44 mmol) of 2-phenyl-thioindoxyl, 16 g (270 mmol) of acetamide and 4.2 g (70 mmol) of acetic acid is stirred for 24 hours at a bath temperature of 200° C. After cooling, the reaction mixture is diluted with methylene chloride, washed in water and dilute ammonia, the organic phase is dried over a mixture of $Na_2SO_4$ and active charcoal and evaporated. The residue is re-crystallised in acetic acid: 5.2 g (44% of theory) of 3-acetamido-2-phenyl-benzo(b)thiophene, colourless crystals melting between 219° and 221° C. ($CHCl_3$).

EXAMPLE 7

3-ethylamino-2-phenyl-benzo(b)thiophene.

10.7 g (40 mmol) of 3-acetamido-2-phenyl-benzo(b)thiophene and 3.8 g (0.1 mol) of $LiAlH_4$ in 200 milliliters of absolute dioxan is refluxed with stirring for 1 hour. The cooled reaction mixture is mixed with water to decompose the excess $LiAlH_4$ and, after the addition of 300 milliliters of $CH_2Cl_2$, it is stirred for a further 15 minutes. After centrifuging with the addition of hyflo, the organic phase is dried over potassium carbonate and evaporated: 3-ethylamino-2-phenyl-benzo(b)thiophene in the form of a crude oily product. It is dissolved in a little chloroform and converted into the hydrochloride by hydrochloric gas: 10.9 g (94% of theory) of colourless sticks in ethanol, decomposition from 205° C. (in sealed tube).

EXAMPLE 8

3-N-formyl-N-methylamino-2-phenyl-benzo(b)thiophene.

A mixture of 75.0 g (0.33 mol) of 2-phenyl-thioindoxyl, 75 milliliters (1.27 mol) of N-methyl formamide and 20 milliliters of formic acid at 98% (0.52 mol) is refluxed for 8 hours. After cooling, it is diluted with $CH_2Cl_2$ and washed in water. By evaporating the organic phase dried over sodium sulphate, 87.6 g (99% of theory) of N-formyl-N-methylamino-2-phenyl benzo(b)thiophene are obtained: colourless crystals melting between 132° and 134° C. (benzene).

EXAMPLE 9

3-methylamino-2-pheny-benzo(b)thiophene.

34.2 g (0.13 mol) of 3-formamido-3-methylamino-2-phenyl-benzo(b)thiophene are refluxed with stirring for 4 hours with 300 milliliters of HCl at 25%. After cooling, it is diluted in water, made alkaline by sodium hydroxide solution and stirred with $CH_2Cl_2$. After the organic phase has been extracted several times 2 N NaOH 7.4 g (26% of theory) of 2-phenyl-thioindole are isolated. By evaporating the solution of $CH_2Cl_2$ dried over $K_2CO_3$, the 3-methylamino-2-phenyl-benzo(b)thiophene is obtained in the form of a crude oily product. It is dissolved in a little $CHCl_3$ and converted into the hydrochloride by hydrochloric gas: 20.2 g (57% of theory) of colourless prisms in a mixture of ethanol and ether, decomposition from 198° C. (in a sealed tube).

EXAMPLE 10

3-(N-methyl-N-propylamino)-2-phenyl-benzo(b)thiophene.

11.45 g (0.303 mol) of $NaBH_4$ are suspended in a solution of 14.5 g (60.6 mmol) of 3-methylamino-2-phenyl-benzo(b)thiophene in 150 milliliters of absolute benzene. With stirring and cooling by ice water, 78.3 milliliters (1.06 mol) of propionic acid are added dropwise sufficiently slowly for the temperature not to exceed 20° C. When this addition is completed, the mixture is refluxed for a further 30 minutes. The cooled reaction mixture is mixed at 70° C. with approximately 200 milliliters of water and neutralised with caustic soda. By evaporating the organic phase dried over $K_2CO_3$, the 3-N-methylamino-N-propylamino-2-phenylbenzo(b)thiophene is obtained in the form of a crude oily product. It is re-crystallised by trituration with methanol: 12.0 g (70% of theory), colourless crystals melting between 52° and 53° C. (methanol).

Preparation of the starting product by reduction of the 3-formamido-2-phenyl-benzo(b)thiophene which can be isolated either by drying of the intermediate product formed from preparation of the 3-amino-2-phenyl-benzo(b)thiophene from the 2-phenyl-benzo(b)thiophen-3-ol produced as an intermediate product (described following Example 14) by heating for 1 hour the 3-amino-2-phenyl-benzo(b)thiophene with the same quantity of formic acid at 98 to 100%, followed by dissolving in water and drying. In both cases, 3-formamido-2-phenyl-benzo(b)thiophene is obtained in a quantitative yield: thin colourless needles, mp 185°–186° C. (benzene). 3.0 g (11.8 mmol) of this amide and 1.08 g (28.4 mmol) of LiAlH$_4$ in 60 milliliters of absolute dioxan are refluxed with stirring for 30 minutes. Water is added to the cooled reaction mixture to decompose the excess LiAlH$_4$ and, after the addition of approximately 100 milliliters of CH$_2$Cl$_2$, it is stirred for a further 15 minutes. After centrifuging with the addition of a filtration aid the organic phase is dried over K$_2$CO$_3$ and evaporated. The hydrochloride of the solution of the residue is precipitated in a little chloroform by the action of hydrochloric gas: 2.6 g (80% of theory). The hydrochloride of 3-methylamino-2-phenyl(b)thiophene, colourless crystals in ethanol-ether, decomposition from 198° C. (in sealed tube). From this salt the base is released by the action of ammonia: 3-methylamino-2-phenyl -benzo(b)thiophene, yellow rods, mp 78°–79° C. (methanol).

EXAMPLE 11

3-N-formyl-N-hexylamino-2-phenyl-benzo(b)thiophene.

A mixture of 10.0 g (44 mmol) of 2-phenyl-thioindoxyl, 18 g (140 mmol) of N-hexylformamide and 6 milliliters (160 mmol) of formic acid is heated to 190° for 15 days. 20 milliliters of formic acid are then added and refluxed for a further hour. After elimination of the volatile material under reduced pressure, there remain 14.8 g (99% of theory) of 3-N-formyl-N-hexylamino-2-phenyl- benzo(b)thiophene in the form of a crude oily product. It is saponified without any other purification in the corresponding secondary amine.

EXAMPLE 12

3-hexylamino-2-phenyl-benzo(b)thiophene.

14.6g (43 mmol) of the compound prepared in Example 11 are refluxed for 12 hours with 200 milliliters of HCl at 25%. After cooling, the mixture is diluted with water, made alkaline with concentrated NaOH and stirred with CH$_2$Cl$_2$. After the organic phase has been extracted several times with 2 N NaOH 1.8 g (18% of theory) of the phenyl-2-thioindoxyl are isolated. The oil remaining after evaporation of the solution of CH$_2$Cl$_2$ dried over K$_2$CO$_3$ is dissolved in a little chloroform and converted into the hydrochloride by hydrochloric gas: 6.1 g (41% of theory) of 3-hexylamino-2-phenyl-benzo(b)thiophene, colourless crystals in ethanol-ether, decomposition from 142° (in sealed tube).

EXAMPLE 13

3-N-dimethylamino-2-phenyl-benzo(b)thiophene.

12.0 g (53 mmol) of 3-amino-2-phenyl-benzo(b)thiophene are refluxed with stirring for 2 hours at the same time as 12 g of formalin at 35% (0.14 mol) and 12 g of formic acid at 98 to 100% (0.26 mol). The cooled reaction mixture is poured into water, made alkaline by ammonia and extracted with CH$_2$Cl$_2$. Evaporation of the organic phase dried over K$_2$CO$_3$ gives the 3-dimethylamino-2-phenyl-benzo(b)thiophene in the form of a crude oily product.

This oil crystallises in contact with methanol: 9.5 g (71% of theory), yellow rods, , mp 84° to 86° (methanol).

The starting material can be prepared according to one or other of the processes described under a and b below.

(a) mixture of 60.0 g (0.265 mol) of 2-phenyl-benzo(b)thiophen-3-ol(prepared according to L. KALB and J. BAYER, Ber. dtsch. chem. Ges. 46, 3879 (1913), 60 milliliters (1.51 mol) of formamide and 16 milliliters (0.42 mol) of formic acid at 98 to 100% is refluxed with stirring for 24 hours at a bath temperature of 190° C. The still hot reaction mixture is poured into water, the precipitated solid product is centrifuged and refluxed with stirring for 8 hours with 700 milliliters of HCl at 25%. The cooled reaction mixture is diluted in water, neutralised by ammonia and the product dissolved with CH$_2$Cl$_2$. By evaporating the organic phase dried over K$_2$CO$_3$, 58.7 g (98% of theory) of 3-amino-2-phenyl-benzo(b)thiophene are obtained: yellow plates, mp 110°–112° C. (cyclohexane).

(b) from 10.5 g (84 mmol) of benzylmercaptan and the equimolar quantity of sodium methoxide the corresponding salt is prepared. A solution of sodium benzylthiolate is stirred for 1 hour at ambient temperature in 150 milliliters of absolute dimethyl formamide after the addition of 10.5 g (76 mmol) of 2-chloro-benzonitrile and 8.0 g of a disbursion of NaH at 50% (0.167 mol). The mixture is then poured into water and the product extracted with CH$_2$Cl$_2$. By evaporating the organic phase dried over Na$_2$SO$_4$ and re-crystallising the residue in cyclohexane, 16.0 g (93% of theory) of 3-amino-2-phenyl—benzo(b)thiophene are obtained, yellow plates, mp 110°–112° C.

EXAMPLE 14

3-dimethylamino-2-phenyl-benzo(b)thiophene.

In a solution of 22.5 grams (100 mmol) of 3-amino-2-phenyl—benzo(b)thiophene in 700 milliliters of absolute tetrahydrofuran are suspended 37.8 grams (1 mol) of NaBH$_4$ and 180 grams (3.9 mol) of formic acid are added slowly dropwise with stirring and cooling so that the temperature does not exceed 5°. After heating to ambient temperature the mixture is refluxed for 30 minutes, the cooled reaction mixture is mixed at 50° with water and made alkaline by the addition of caustic soda. After the ether extract is dried and evaporated, the residue is dissolved in 100 milliliters of methylene chloride and 10 milliliters of acetic anhydride are added. The final acetylated product is centrifuged, the filtrate is washed with ammonia, dried over K$_2$CO$_3$ and evaporated: 3-dimethylamino-2-phenyl-benzo(b)thiophene in the form of a crude oily product which is crystallised by trituration with methanol: 11.4 grams (45% of theory) of yellow rods melting between 85° and 87° (methanol).

EXAMPLE 15

3-Dimethylamino-2-phenyl-benzo(b)thiophene.

10 g (44 mmol) of 3-amino-2-phenyl-benzo(b)thiophene are heated to 110° C. with stirring for 14 hours with 100 ml of dimethyl sulphate. After the addition of 300 ml of NaOH at 20% the mixture is refluxed for 2 hours in order to decompose the excess dimethyl sulphate. By extracting the cooled reaction mixture with ether, drying the organic phase over K$_2$CO$_3$ and evaporating, the 3-dimethylamino 2-phenyl-benzo(b)thiophene is obtained in the form of a crude oily product which is crystallised in methanol: 8.1 g (72% of theory) of yellow rods, mp 84°–85° C. (methanol).

EXAMPLE 16

3-Diethylamino-2-phenyl-benzo(b)thiophene.

In a solution of 11.25 g (50 mmol) of 3-amino-2-phenyl-benzo(b)thiophene in 150 ml of absolute benzene are suspended 18.9 g (0.5 mol) of NaBH$_4$ and, with stirring and cooling, 96 ml (1.6 mol) of acetic acid are added dropwise sufficiently slowly for the temperature not to exceed 20°. The mixture is then refluxed with stirring for 30 minutes, cooled to 70° C., mixed carefully with water and made alkaline by caustic soda. After concentrating the organic phase dried over K$_2$CO$_3$, the hydrochloride is formed by the action of hydrochloric gas, 11.9 g (75% of theory) of hydrochloride of 3-dimethylamino-2-phenyl-2-benzo(b)thiophene, colourless prisms in ethanol-ether, decomposition from 178° (in sealed tube).

EXAMPLE 17

3-N-benzylideneamino-2-phenyl-benzo(b)thiophene.

A solution of 15.0 g (67 mmol) of 3-amino-2-phenyl-benzo(b)thiophene and 7.8 g (74 mmol) of benzaldehyde freshly distilled in 50 ml of benzene is refluxed for 10 hours with a water trap. After cooling, it is diluted in benzene, the excess benzaldehyde is eliminated by stirring with a solution of sodium bisulphite, the organic phase is dried over Na$_2$SO$_4$ and evaporated: 3-N-benzylideneamino-2-phenyl-benzo(b)thiophene in the form of a crude oily product. It crystallises in contact with methanol: 19.0 g (91% of theory) of yellow crystals, mp 92°–93° (ethanol).

EXAMPLE 18

3-benzylamino-2-phenyl-benzo(b)thiophene.

9.6 g (31 mmol) of the compound of Example 17 and 12 g (0.32 mol) of NaBH$_4$ in 300 ml of absolute ethanol are refluxed with stirring for 25 hours. The cooled reaction mixture is diluted in water and extracted in ether. By evaporating the organic phase dried over K$_2$CO$_3$, the 3-benzylamino-2-phenyl-benzo(b)thiophene is obtained in the form of a crude oily product. It is dissolved in a little CHCl$_3$ and the hydrochloride is formed by treatment with hydrochloric gas: 10.1 g (94% of theory), colourless crystals in ethanol, decomposition from 170° (in sealed tube).

EXAMPLE 19

3-dibenzylamino-2-phenyl-benzo(b)thiophene.

A mixture of 2.25 g (10 mmol) of 3-amino-2-phenyl benzo(b)thiophene, 3.8 g (22 mmol) of benzyl bromide, 3.6 g (26 mmol) of K$_2$CO$_3$ and 0.5 g (3.3 mmol) of NAI in 25 ml of absolute CHCl$_3$ is refluxed with stirring for 20 hours. After cooling, it is mixed with water, the organic phase is dried and washed with water. After drying over calcium carbonate and elimination of the solvent, there remains 3-dibenzylamino-2-phenyl-benzo(b)thiophene in the form of a crude oily product which crystallises in ethanol: 2.3 g (57% of theory), colourless crystals, mp 97°–101° (ethanol).

EXAMPLE 20

2-(4 chloro-phenyl)-3-formamido-benzo(b) thiophene.

A mixture of 27.5 g (0.105 mol) of 2-(4-chlorophenyl)-benzo(b)thiophen-3-ol, 28 ml (0.7 mol) of formamide and 7.5 ml (0.195 mol) of formic acid at 98% is refluxed with stirring for 20 hours at a bath temperature of 190° C. The still hot reaction mixture is poured into water and triturated in the wet state: 29.5 g (98% of theory) of 2-(4 chlorophenyl)-3-formamido- -benzo(b)-thiophene, colourless needles, mp 216°–217° C. (acetate).

Preparation of the starting material: a solution of 12.7 g (0.23 mol) of KOH in 130 ml of absolute ethanol is mixed with 38.2 g (0.23 mol) of methyl thiosalicylate, then with 49.6 g (0.23 mol) of α-chloro-p-chloro-phenyl acetate (prepared according to W. Baker, W. P. Oelis and V. D. Poole, J. Chem. Soc. 1950, 1547). After reflux for 30 minutes the mixture is poured into water and the oil formed in CH$_2$Cl$_2$ is recovered. By evaporating the organic phase dried over sodium sulphate and re-crystallising in a mixture of petroleum ether and benzene, 59.9 g (75% of theory) of methyl[α-(2-methoxycarbonyl) phenylthio-p-chloro] phenyl acetate are obtained, colourless crystals, mp 74°–75°.

To a solution of sodium hydrate prepared from 7.9 g (0.34 gram atom) of sodium at 100 ml of absolute ethanol is added dropwise for 30 minutes with stirring a solution of 65.5 g (0.17 mol) of the diester described above in 450 ml of absolute ether, then refluxed with stirring for a further 45 minutes. The cooled reaction mixture is poured into water, acidified with concentrated HCl, the organic layer is separated and the aqueous phase is extracted again with ether. By evaporating the organic phase dried over sodium sulphate and re-crystallising in a mixture of petroleum ether and benzene, 28.2 g (63% of theory) of 2-(4-chlorophenyl)-benzo(b)thiophen-3-ol are obtained, colourless needles, mp 132°–134° C.

EXAMPLE 21

3-Dimethylamino-2-(4-chlorophenyl)-2-benzo(b) thiophene.

15.0 g (58 mmol) of 2-(4 chlorophenyl)-3-aminobenzo(b)thiophene and 15 ml of formic acid at 98% (390 mmol) are refluxed with stirring for 2 hours. The cooled reaction mixture is poured onto water, made alkaline with caustic soda and extracted with CH$_2$Cl$_2$. After the organic phase has been dried over potassium carbonate and the solvent eliminated, there remain 15.9 g (96% of theory) of 3-dimethylamino-2-(4-chlorophenyl)-benzo(b)thiophene yellow crystals, mp. 114°–116° (ethanol).

Preparation of the starting material: 29.5 g (0.103 mol) of 3-formamido-2-(4'-chloro-phenyl) benzo(b)thiophene with 300 ml of hydrochloric acid at 25% are refluxed with stirring for 10 hours. After cooling, the mixture is poured into water, made alkaline by ammonia and extracted with CH$_2$Cl$_2$. By evaporating the organic phase dried over K$_2$CO$_3$ and recrystallising the residue in acetone, 19.9 g (73% of theory) of 3-amino-2-(4-chlorophenyl)-benzo(b)-thiophene are obtained, yellow crystals, mp. 152°–154° (benzene).

EXAMPLE 22

3-bis(2 chloro-ethyl)amino-2-phenyl-benzo(b)thiophene.

620 g (6.6 mol) of chloroacetic acid are added to 1½ l of absolute benzene and, by stirring and cooling, 75.6 g (2 mol) of NaBH$_4$ are added in portions sufficiently slowly for the temperature not to exceed 20°. After the addition of 45.1 g (0.2 mol) of 3-amino-2-phenyl-benzo(b)-thiophene, the mixture is refluxed with stirring for 30 minutes. The still hot reaction mixture is mixed by stirring with 1½ l of water and neutralised with Na$_2$CO$_3$. By evaporating the organic phase dried over K$_2$CO$_3$ and recrystallising the residue in ethanol, 49.6 g (71% of theory) of 3-bis(-2-chloro-ethyl)amino-2-phenyl-benzo(b)thiophene thiophene are obtained, colourless needles mp. 108°–110°.

EXAMPLE 23

3-(4-methylpiperazino)-2-phenyl-benzo(b)thiophene.

A solution of 3.5 g (10 mmol) of the compound prepared in Example 22 in 20 ml of absolute tetrahydrofuran is placed in an autoclave and cooled to −60°. After the addition of approximately 3 g (approximately 100 mmol) of methylamine which has first been liquified by cooling, the reaction vessel is closed and heated to 100° for 90 hours. After mixing with water, it is extracted with ether, the organic phase dried over $K_2CO_3$ and evaporated: 3-(4-Methylpiperazino)-2-phenyl-benzo(b)-thiophene in the form of a crude oily product. By triturating with methanol 2.05 g (67% of theory) of beige crystals melting at 119°–121° (methanol) are obtained.

EXAMPLE 24

3-(4-benzylpiperazino)-2-phenyl-benzo(b) thiophene.

A mixture of 40.0 g (0.114 mole) of the compound of Example 22, 40 g (0.374 mole) of benzylamine and 60 milliliters of diphenyl ether is heated to 160° with stirring for 7 hours. The cooled reaction mixture is distributed between chloroform and water and the organic phase is driedover a $K_2CO_3$ and thoroughly concentrated. The base of the hydrochloride formed by action of hydrochloric gas and filtration is released 32.4 g (74% of theory) of 3-(4-benzylpiperazino)-2-phenyl-benzo(b)thiophene, colourless needles, mp 121°–123° (ethanol-acetone).

EXAMPLE 25

3-(4-ethoxycarbonylpiperazino)-2-phenyl-benzo(b)-thiophene.

A solution at 70° of 26.7 g (69.5 mmoles) of the compound of Example 24 in 270 milliliters of absolute benzene is poured dropwise for 30 minutes into 15.1 g (0.139 mole) of ethyl chloroformade in 60 milliliters of absolute benzene and the reaction mixture is refluxed for a further 4 hours. By eliminating the solvent under reduced pressure the 3-(4-ethoxycarbonylpiperazino)-2-phenyl-benzo(b)-thiophene is obtained in the form of a crude oily product. It is triturated with petroleum ether: 24.5 g (96% of theory) of colourless crystals, mp 115°–116° C. (methanol).

EXAMPLE 26

3-(piperamino)-2-phenyl-benzo(b)thiophene.

16.2 g (44 mmoles) of the compound of Example 25, 16 g of KOH and 20 milliliters of ethanol are heated for 2½ hours to about temperature of 120° C. with occasional stirring. After cooling, the mixture is poured onto water and centrifuged. The ethanol solution of solid substances is diluted with $CH_2Cl_2$, the organic phase is separated and dried over $K_2CO_3$: 3-piperazino-2-phenyl-benzo(b)thiophene in the form of a crude oily product. This product is crystallised by trituration with petroleum ether: 11.9 g (92% of theory) of colourless crystal.

EXAMPLE 27

3-(4-acetylpiperazino)-2-phenyl-benzo(b)thiophene.

6.15 g (60 mmole) of acetic anhydride are mixed with a solution of 11.8 g (40 mmole) of 3-piperazino-2-phenyl-benzo(b)thiophene in 50 milliliters of methylene chloride and left for 2 hours at ambient temperature. After washing with dilute ammonia the organic phase is dried over $Na_2SO_4$ and evaporated: 13.2 g (98% of theory) of colourless needles, mp 167°–169° ($CCl_4$).

EXAMPLE 28

3-(4-methylpiperazino)-2-phenyl-benzo(b)thiophene.

A mixture of 7.0 g (24 mmole) of 3-(piperazino)-2-phenyl-benzo(b)thiophene, 3.5 milliliters of formalin at 35% (41 mmole) and 3.5 milliliters of formic acid at 98–100% (92 mmole) is refluxed for 1 hour. After cooling, it is poured into water, made alkaline with ammonia and extracted with $CH_2Cl_2$. By evaporating the organic phase dried over $K_2CO_3$, 7.2 g (98% of theory) of 3-(4'-methylpiperazino)-2-phenyl-benzo(b)thiophene are obtained: beige crystals, mp 118°–120° (methanol).

EXAMPLE 29

3-dimethylamino-2-phenyl-benzo(b)thiophene.

A solution of 14.4 g (53 mmole) of the dimethylamide of α-phenylthio-phenylacetic acid, 24.5 milliliters (160 mmole) of $POCl_3$ in 250 milliliters of absolute toluene is refluxed for 6 hours. After mixing with water, it is neutralised with ammonia and the organic phase is dried over a mixture of $K_2CO_3$ and activated charcoal and evaporated: 3-dimethylamino-2-phenyl-benzo(b)thiophene in the form of a crude oily produce which, triturated with methanol, yields 11.1 g (83% of theory) of colourless rods, mp 84°–85° (methanol).

Preparation of the starting material: 24.5 g (0.1 mole) of α-phenylthio-phenylacetic acid and 25 milliliters (0.34 mole) of $SOCl_2$ are refluxed for 2 hours. After the excess $SOCl_2$ has been removed, the crude acid chloride is dissolved in 200 milliliters of dioxan and, with stirring and cooling, 52 milliliters (0.4 mole) of an aqueous solution at 40% of dimethylamine are added dropwise. After dilution with water the mixture is extracted with $CH_2Cl_2$. By evaporating the organic phase dried over $Na_2SO_4$, 26.2 g (96% of theory) of the N,N-dimethyl-(α,phenylthioα,phenyl)acetamide are obtained: colourless plates, mp 109°–111° (benzene/petroleum ether).

EXAMPLE 30

5-chloro-3-piperidino-2-phenyl-benzo(b)thiophene.

A solution of 16.5 g (47 mmole) of N-[(α-4-chloro-phenylthio)-phenylacetyl] piperidine and 13 milliliters (142 mmole) of $POCl_3$ in 200 milliliters of absolute toluene is refluxed for 8 hours. After mixing with water, it is neutralised with ammonia and the organic phase is dried over a mixture of potassium carbonate and activated charcoal and evaporated: 14.4 g (74% of theory) of 5-chloro-3-dimethylamino-2-phenyl-benzo(b)thiophene, yellow rods, mp 115°–116° (ethanol).

Preparation of the starting material: 20 g (72 mmole) of α-(4-chlorophenylthio)-phenylacetic acid and 20 milliliters (280 mmole) of $SOCl_2$ are refluxed for 3 hours. After the excess $SOCl_2$ has been removed, the crude acid chloride is dissolved in 100 milliliters of dioxan and, with stirring the cooling, 21.2 milliliters (290 mmole) of piperidine are added dropwise. After dilution in water, the mixture is extracted with $CH_2Cl_2$. By evaporating the organic phase dried over $Na_2SO_4$, 22.6 g (91% theory) of the piperidinium salt of α-(4-chlorophenylthio)-phenylacetic acid are obtained: colourless rods, mp 125°–126° (benzene/petroleum ether).

EXAMPLE 31

3-dimethylamino-2-(4 chlorophenyl)benzo(b)thiophene.

A solution of 15.3 g (50 mmol) of the dimethylamide of α-phenylthio-p-chloro-phenylacetic acid (colourless rods in a mixture of petroleum ether and benzene, mp 81°–83°) and of 23.0 g (150 mmol) of POCl$_3$ in 160 milliliters of chlorobenzene is refluxed for 6 hours. By treatment similar to that of Example 29 the 3-dimethylamino-2-(4-chloro-phenyl)-benzo(b)thiophene is obtained in the form of a crude oily product which crystallises after trituration with ethanol: 11.1 g (77% of theory), yellow rods, mp 114°–116° (ethanol).

EXAMPLE 32

3-(4-methyl-piperazino)-2-phenyl-benzo(b)-thiophene.

Proceed as in Example 31, starting from the 1-methyl-4-(α-phenylthioacetyl)-piperazine acid (T.C. ASTHANA and Coll.l.c), duration of reaction 3 hours, 63% of theory, beige crystals mp 119°–121° (methanol).

EXAMPLE 33

Hydrochloride of 3-diethylamino-2-phenyl-benzo(b)-thiophene.

Proceed as in Example 31 starting from the N,N-diethyl-(α-phenyl-α-phenylthio)-acetamide (T.C. ASTHANA and Coll., l.c.), duration of reaction 7 hours. The crude oily product constituting the base is dissolved in an equal quantity of CHCl$_3$ and converted into the hydrochloride by the action of hydrochloric gas. The hydrochloride crystallises after the addition of ether: 81% of theory of hydrochloride of 3-dimethylamino-2-phenylbenzo(b)thiophene, colourless prisms in ethanol-ether, decomposition from 178° (in sealed tube).

EXAMPLE 34

Hydrochloride of 3-(pyrrolidino)-2-phenyl-benzo(b)-thiophene.

Proceed as in Example 33 starting from the N-(α,phenyl-α,phenyl-thioacetyl)-pyrrolidine (T.C. ASTHANA and Coll, l.c.), duration of reaction 2 hours. 66% of theory of colourless needles in a mixture of ethanol and ether, decomposition from 166° (in sealed tube).

EXAMPLE 35

Hydrochloride of 3-(piperidino)-2-phenyl-benzo(b)-thiophene.

Proceed as in Example 29 starting from the N-(α,-phenylα, phenylthioacetyl)piperidine (T.C. ASTHANA and Coll,l.c.), duration of reaction 10 hours. It is converted into the hydrochloride in a manner similar to that of Example 33; 59% of theory of yellow crystals in a mixture of ethanol and ether, decomposition from 160° (in sealed tube).

EXAMPLE 36

5-chloro-3-dimethylamino-2-phenylbenzo(b)thiophene.

Proceed as in Example 31 starting from the N,N-dimethyl [α-(4-chloro-phenylthio)-α-phenyl]-acetamide (colourless rods, in a mixture of benzene and petroleum ether, mp 114°–116°), duration of reaction 3 hours, 60% of theory of colourless rods, mp. 79°–81° (methanol).

EXAMPLE 37

Hydrochloride of 2-(4-chlorophenyl)-3-diethylamino-benzo(b)thiophene.

Proceed as in Example 33 starting from the N,N-diethyl-(α-phenylthio)-α-(4-chlorophenyl)acetamide (colourless rods in methanol, mp. 82°–83°), duration of reaction 8 hours. 75% of theory of beige crystals in a mixture of methanol and ether, decomposition from 120° (in sealed tube).

EXAMPLE 38

2-(4-chlorophenyl)-3-di-n-butylaminobenzo(b)-thiophene.

Proceed as in Example 31 starting from the N,N-di(n-butyl) [α-phenylthioα-(4-chlorophenyl] acetamide (yellow oil boiling between 180° and 185° at 0.05 torr). The duration of reaction is 9 hours. 50% of theory of colourless prisms melting between 48° and 50° (methanol) are obtained.

EXAMPLE 39

3-dimethylamino-2-(4-methoxyphenyl)-benzo(b)-thiophene.

Proceed as in Example 31 starting from the N,N-dimethyl [α,phenylthio-α-(4-methoxy)-phenyl] acetamide (colourless needles in benzene and petroleum ether, mp 60°–61°). The duration of the reaction is 3 hours. 45% of theory of colourless crystals melting between 163° and 165° (acetate) are obtained.

EXAMPLE 40

3-dimethylamino-5-methyl-2-phenyl-benzo(b)-thiophene.

Proceed as in Example 31 starting from the N,N-dimethyl-α-(4-methylphenylthio)-α-phenylacetamide (colourless crystals in cyclohexane, mp 99°–102°). The duration of reaction is 5 hours. 61% of theory of colourless needles, mp 89°–92° (ethanol).

EXAMPLE 41

3-dimethylamino-5-methylthio-2-phenyl benzo(b)thiophene.

Proceed as in Example 31 starting from the N,N-dimethyl-[2-(4-methylthio)-phenylthio]-α-phenylacetamide (crude product used for cyclisation). The duration of reaction is 25 hours. 42% of theory of slightly yellow crystals melting between 87° and 89° (methanol) are obtained.

EXAMPLE 42

3-(N-butyl,N-methylamino)-2-(4-methoxyphenyl)-benzo(b)thiophene.

Proceed as in Example 31 starting from the N-butyl, N-methyl[α-phenylthio-α-(4-methoxyphenyl)] acetamide (crude product used for cyclisation). The duration of reaction is 3 hours. 45% of theory of beige crystals, mp 61°–62° (methanol).

EXAMPLE 43

2-phenyl-3-phenylamino-benzo(b)thiophene.

A mixture of 9.6 g (30 mmol) of anilide of α-phenylthio-phenylacetic acid (colourless needles in a mixture of benzene and petroleum ether, mp 142°–143°), 70 milliliters of absolute toluene and 30.0 g (211 mmol) of phosphoric anhydride is stirred at 100° for 8 hours. The cooled reaction mixture is poured onto ice, made alkaline by concentrated ammonia and extracted with methylene chloride. By drying over sodium sulphate and evaporating the organic phase, 8.9 g (98.4% of theory) of crude product are obtained which are recrystallised in ethanol: 5.7 g (64% of theory) of yellow crystals, mp 150°–151° (ethanol).

EXAMPLE 44:

2-phenyl-3-phenylamino-benzo(b)thiophene.

3.0 g of anilide of phenylthio-phenyl acetic acid (colourless needles in a mixture of benzene and petroleum ether mp 142°–143°) in 130 g of polyphosphoric acid are heated to 100° for 19 hours. The cooled reaction mixture is poured onto water, made alkaline by concentrated ammonia and extracted with methylene chloride. By drying over sodium sulphate and evaporating the extracts of methylene chloride, 1.7 g (60.0% of theory) of yellow oil are obtained which are recrystallized in ethanol: 1.5 g (45% of theory) of yellow crystals, mp 150°–151° (ethanol).

EXAMPLE 45

5-bromo-2-phenyl-3-(4-benzylpiperazino)benzo(b)thiophene.

Proceed as in Example 31 starting from the N'-benzylpiperazide of α-(4'-bromophenylthio)-phenylacetic acid (colourless crystals in methanol, mp 115°–117°). The duration of reaction is 40 hours. 87.2% of theory, colourless needles, mp 156°–157° (methanol).

EXAMPLE 46

2-(4-chlorophenyl)-3-morpholino-benzo(b)thiophene.

Proceed as in Example 31 starting from the N-[(α-phenylthio)α(4-chlorophenyl)ethyl] morpholine (colourless prisms in a mixture of benzene and petroleum ether, mp. 118°–119°). The duration of reaction is 3½ hours, 57% of theory of beige crystals, mp. 140°–141° (ethanol-benzene).

EXAMPLE 47

3-dibenzylamino-2-phenyl-benzo(b)thiophene.

40.2 g (0.33 mol) of benzoic acid are added to 100 milliliters of absolute benzene and, by cooling and stirring, 3.78 g (0.1 mol) of $NaBH_4$ are added in portions sufficiently slowly for the temperature not to exceed 20° C. After the addition of 6.3 g (20 mmol) of 3-benzylamino-2-phenyl-benzo(b)thiophene the mixture is refluxed for 60 minutes. The still hot reaction mixture has added to it by stirring half a liter of water and is neutralised by ammonia. By evaporating the organic phase dried over $K_2CO_3$ and recrystallising the residue in ethanol, 5.1 g (41% of theory) of 3-dibenzylamino-2-phenyl-benzo(b)thiophene are obtained, colourless crystals, mp 98°–100° C.

Preparation of the starting material a solution of 15.0 g (67 mmol) of 3-amino-2-phenyl-benzo(b)thiophene and 7.8 g (74 mmol) of benzaldehyde freshly distilled in 50 milliliters of benzene is refluxed for 10 hours with a water trap. After cooling, it is diluted with benzene, the excess benzaldehyde is eliminated by stirring with a solution of sodium bisulphite, the organic phase is dried over $Na_2SO_4$ and evaporated: 3-benzylidenamino-2-phenyl-benzo(b)thiophene in the form of a crude oily product which crystallises when it is triturated with methanol: 19.0 g (91% of theory) of yellow crystals, mp 92°–93° C. (ethanol). 9.6 g (31 mmol) of this Schiff base and 12 g (0.32 mol) of $NaBH_4$ in 300 milliliters of absolute ethanol are refluxed with stirring for 25 hours. The cooled reaction mixture is diluted in water and extracted with ether. By evaporating the organic phase dried over $K_2CO_3$, the 3-benzylamino-2-phenyl-benzo(b)thiophene is obtained in the form of a crude oily product which crystallises when it is triturated with methanol. 9.0 g (92% of theory), colourless crystals, mp 52°–53° C. (methanol).

EXAMPLE 48:

3-dimethylamino-4-phenyl-benzo(b)thiophene.

By reacting 3-methylamino-2-phenyl-benzo(b)thiophene with dimethylsulphate, 4.8 g (20 mmol) of 3-methylamino-2-phenyl benzo(b)thiophene with 30 milliliters of dimethylsulphate are heated to 110° C. with stirring for 10 hours; after the addition of 100 milliliters of NaOH at 20% the mixture is refluxed for 2 hours to destroy the excess dimethylsulphate. The cooled reaction mixture is extracted with ether and the organic phase is dried over $K_2CO_3$ and evaporated to obtain the 3-dimethylamino-phenyl-benzo(b)thiophene in the form of a crude oily product which crystallises when triturated with methanol: 4.0 g (79% of theory) of yellow rods mp 85°–86° C. (methanol).

EXAMPLE 49

3-dibenzylamino-2-phenyl-benzo(b)thiophene starting from 3-benzylamino-2-phenyl-benzo(b)thiophene.

6.3 g (20 mmol) of 3-benzylamino-2-phenyl-benzo(b)thiophene are refluxed with stirring for 15 hours, at the same time as 4.0 g (23 mmol) of benzyl bromide, 4.0 g (29 mmol) of $K_2CO_3$ and 0.5 g (3.3 mmol) of NaI in 60 milliliters of absolute chloroform. After cooling the mixture is poured onto water, the organic phase is separated and washed with water. By drying over $K_2CO_3$ and eliminating the solvent, the 3-benzylamino-2-phenyl-benzo(b)thiophene is obtained in the form of a crude oily product which crystallises when triturated with ethanol: 5.1 g (63% of theory) of colourless crystals, mp 97°–100° C. (ethanol). The results of the toxicological and pharmacological tests which are listed below reveal the high tolerance and activities of the derivatives of the invention, notably hypolipemiant and hypocholesterolemiant activities.

The object of the invention is therefore also a medicine having, in particular, hypolipemiant and hypocholesterolemiant activities, characterised in that it contains as active substance a compound of formula I or a pharmaceutically compatible acid addition salt or a quarternary ammonium derivative of a derivative of formula I.

TOXICOLOGICAL STUDY

This study has revealed the low toxicity of the derivatives of the invention.

Acute toxicity was determined orally in the rat and mouse by the method of Miller and Tainter: The $LD_{50}$/24H/Hg of body weight is above 4 g for all the derivatives.

Sub-acute toxicity by the oral method was studied for 3 and 6 weeks in the rat and 4 weeks in the dog. Experiments related to the study of growth and weight behaviour, food and water needs, hematological and biochemical examinations, macroscopic (weight and state of organs) and microscopic (histopathology) examination after death.

These experiments showed that the derivatives of the invention were tolerated extremely well throughout the various tests.

PHARMACOLOGICAL STUDY

These experiments revealing the definite hypocholesterolemiant and hypolipemiant action of the compounds of the invention were conducted by two methods.

1 In the Rabbit

The animals divided into several batches of 15 animals are fed with feedstuff enriched in cholesterol (1%). Batch A serves as control and is not treated, the other batches also receive the derivatives to be tested at a dose of 100 mg/Kg, administered orally, suspended in aqueous solution of gum arabic at 5%. On the first day of experimentation and then every 15 days for 75 days biological examinations are conducted on all the animals, during which the various elements causing dyslipemia are dosed; total cholesterol (T), esterified cholesterol (E), free cholesterol (L), esterification ratio (E/T), Kunkel-Phenol test (K1), Kunkelphenol test (K2), Burstein dextrane test (B) and serum lipids (LS).

At the end of the test all the animals are killed and an autopsy is carried out; a macroscopic examination is then conducted on the livers and aortas and a mark of 0 to 3 is given to the amount of fatty infiltrations of the liver and 0 to 4 to the intensity of aortic atheromatous lesions.

The results relating to the most active derivatives and representing average values established within each batch are listed in the following tables:

1st DAY

| batches | T | E | L | E/T | K1 | K2 | B | LS |
|---|---|---|---|---|---|---|---|---|
| A Control | 0,52 | 0,27 | 0,25 | 0,51 | 7,8 | 12,4 | 10,5 | 2,1 |
| B derivative n° 1 | 0,52 | 0,28 | 0,24 | 0,53 | 7,9 | 12,8 | 10,8 | 1,98 |
| C derivative 29 | 0,58 | 0,27 | 0,28 | 0,46 | 7,8 | 12,7 | 10,7 | 1,95 |
| D derivative 37 | 0,57 | 0,27 | 0,30 | 0,47 | 8,2 | 12,9 | 10,5 | 2,00 |
| E derivative 42 | 0,51 | 0,26 | 0,25 | 0,50 | 8,1 | 13,7 | 11,2 | 2,05 |
| F derivative 19 | 0,57 | 0,28 | 0,29 | 0,50 | 8,0 | 13,1 | 10,9 | 1,97 |
| G derivative 24 | 0,55 | 0,28 | 0,27 | 0,50 | 8,2 | 13,0 | 10,8 | 2,00 |

30th DAY

| batches | T | E | L | E/T | K1 | K2 | B | LS |
|---|---|---|---|---|---|---|---|---|
| A Control | 2,35 | 1,50 | 0,85 | 0,63 | 21,8 | 31,9 | 26,8 | 3,90 |
| B derivative n° 1 | 1,50 | 0,95 | 0,55 | 0,63 | 18,8 | 25,7 | 21,3 | 2,9 |
| C derivative 29 | 1,48 | 0,89 | 0,59 | 0,60 | 18,4 | 24,9 | 21,00 | 2,83 |
| D derivative 37 | 1,55 | 0,97 | 0,58 | 0,62 | 18,8 | 25,1 | 21,3 | 2,85 |
| E derivative 42 | 1,45 | 0,90 | 0,55 | 0,62 | 18,9 | 25,5 | 21,2 | 2,91 |
| F derivative 19 | 1,47 | 0,95 | 0,52 | 0,64 | 18,4 | 25,3 | 2,3 | 2,84 |
| G derivative 24 | 1,50 | 0,98 | 0,52 | 0,65 | 18,8 | 25,3 | 2,1 | 2,87 |

75TH DAY

| batches | T | E | L | E/T | K1 | K2 | B | LS |
|---|---|---|---|---|---|---|---|---|
| A Control | 3,71 | 2,30 | 1,41 | 0,61 | 43,8 | 67,1 | 52,3 | 5,85 |
| B derivative n° 1 | 2,96 | 1,84 | 1,12 | 0,62 | 33,3 | 44,2 | 36,2 | 4,18 |
| C derivative 29 | 2,90 | 1,75 | 1,15 | 0,60 | 32,6 | 41,5 | 35,1 | 3,95 |
| D derivative 37 | 2,94 | 1,80 | 1,14 | 0,61 | 32,8 | 46,7 | 35,7 | 4,15 |
| E derivative 42 | 2,94 | 1,85 | 1,09 | 0,61 | 33,2 | 45,0 | 35,4 | 4,05 |
| F derivative 19 | 2,91 | 1,79 | 1,12 | 0,61 | 33,5 | 46,5 | 36,1 | 4,08 |
| G derivative 24 | 2,91 | 1,80 | 1,11 | 0,61 | 32,9 | 48,2 | 35,2 | 3,98 |

| batches | fatty infiltrations of the liver | aortic atheromatons lesions |
|---|---|---|
| A Control | 2,9 | 3,5 |
| B derivative n° 1 | 1,1 | 1,6 |
| C derivative 29 | 0,8 | 1,1 |
| D derivative 37 | 1,00 | 1,3 |
| E derivative 42 | 0,9 | 1,5 |
| F derivative 19 | 1,2 | 1,3 |
| G derivative 24 | 1,00 | 1,4 |

2 In the Rat

Experiments were carried out according to the propylthiouracil test (RANNEY & Coll., J. PHARMACOL. EXPER. THERAP. 1963, 142, 132-136). The propyl-thiouracil administered to adult rats has the property of making them hypercholesterolemic: the plasma level of cholesterol increases by approximately 15% under these conditions. Experiments are conducted on various batches of rats, the control batch receiving only propylthiouracil and the other treated batches also receiving the composition of the invention at an oral dose of 100 mg/Kg.

On the 11th day of experimentation blood samples are taken and the free cholesterol and total cholesterol is dosed. It is established that in the animals treated the cholesterol levels are definitely reduced in relation to the control animals.

The results obtained are listed in the following table:

|  | Free cholesterol g/l | Total cholesterol g/l |
|---|---|---|
| Control (batch A) | 0,23 | 0,87 |
| derivative n° 1 (batch B) | 0,15 | 0,61 |
| derivative n° 29 (batch C) | 0,12 | 0,50 |
| derivative n° 37 (batch D) | 0,13 | 0,58 |
| derivative n° 42 (batch E) | 0,12 | 0,54 |
| derivative n° 19 (batch F) | 0,14 | 0,58 |
| dderivative n° 24 (batch G) | 0,14 | 0,56 |

The results which have just been listed indicate, on the one hand, the high tolerance of the derivatives of the invention and, on the other, their hypocholesterolemiant and hypolipemiant action.

The composition of the invention can be presented for administration by the oral method in the form of tablets, sugar-coated tablets, capsules, drops or syrup. It can also be presented for administration by the rectal method in the form of suppositories and for administration by the parenteral method in the form of an injectable solution.

Each unit dose advantageously contains from 0.050 g to 0.500 g of active substance. Doses administered daily can vary from 0.050 g to 1.5 g of active substance.

Some pharmaceutical formulations of the composition of the invention are given below by way of non-limiting example.

1. TABLETS derivative number 29–0.100 g excipient: wheat starch, talc, potato starch, magnesium stearate.

2. SUGAR-COATED TABLETS derivative number 37–0.100 g excipient: lactose, maize starch, magnesium stearate, ethyl acetate, white wax, purified water, gum arabic, tartrazin yellow, colloidal silica, sugar, talc.

3. CAPSULES derivative number 42–0.150 g excipient: magnesium stearate, talc.

4. SUPPOSITORIES derivative number 19–0.100 g excipient: semi-synthetic triglycerides.

5. INJECTABLE SOLUTION derivative number 24–0.075 g excipient: isotonic solution.

By virtue of its hypocholesterolemiant and hypolipemiant properties the medicament of the invention is usefully employed in therapeutics.

It normalises the blood levels of cholesterol and lipids by regularising their metabolism and thus effectively protects the organism from vascular attacks of atherosclerous origin as well as their complications at cardiac cerebral or peripheral level.

It is indicated in etherogenous hyperlipidemia such as hypercholesterolemia, hypertriglyceridemia, hyperlipidemia and clinical manisfestations of atherosclerous disease such as coronaritis, myocardial infarction, cerebral vascular deficiency, arteritis of the lower limbs, arterial hypertension.

What we claim is:

1. A benzo (b) thiophene of formula:

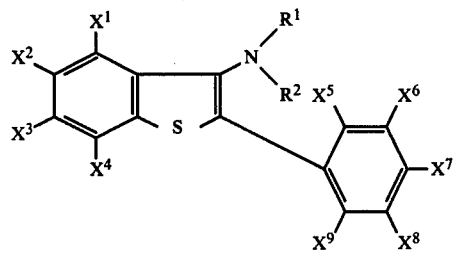

in which $X^1$ to $X^9$ which are identical or different are hydrogen, alkyl having up to 3 carbon atoms, chlorine, bromine, methoxy or methylthio, $R^1$ is hydrogen, alkyl having up to 8 carbon atoms, optionally chlorinated, brominated or methoxylated, phenyl optionally chlorinated or methoxylated, aralkyl having in all up to 9 carbon atoms, optionally chlorinated or methoxylated on the phenyl nucleus, $R^2$ is hydrogen, phenyl, or a radical of formula:

in which A is two hydrogen atoms or one oxygen atom and $R^3$ can have the same meanings as given for $R^1$, $R^1$ and $R^2$ being not both hydrogen, the meanings assumed by $R^1$ and $R^3$ being independent from one another or the group

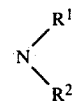

forms the radical piperidino, pyrrolidino, morpholino or piperazino which, in the case of piperazino, can, as appropriate, be substituted on the second nitrogen atom by an alkyl having up to 6 carbon atoms, by an aliphatic or aromatic acyl having up to 8 carbon atoms, by an optionally chlorinated or methoxylated phenyl or by an aralkyl optionally chlorinated or methoxylated on the phenyl nucleus, having in all up to 9 carbon atoms, and the pharmaceutically acceptable salts thereof.

2. A benzo (b) thiophene of formula:

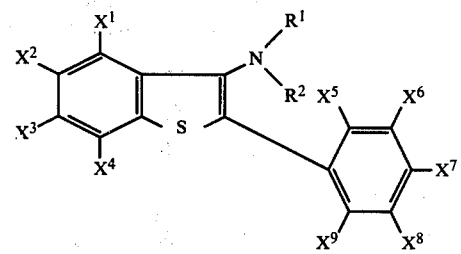

in which $X^1$ to $X^9$ which are identical or different are hydrogen, alkyl having up to 3 carbon atoms, chlorine, bromine, methoxy or methylthio, $R^1$ is hydrogen, alkyl having up to 8 carbon atoms, optionally chlorinated, brominated or methoxylated, phenyl optionally chlorinated or methoxylated, aralkyl having in all up to 9 carbon atoms, optionally chlorinated or methoxylated on the phenyl nucleus, $R^2$ is hydrogen, phenyl, or a radical of formula:

in which A is two hydrogen atoms or one oxygen atom and $R^3$ can have the same meanings as given for $R^1$, $R^1$ and $R^2$ being not both hydrogen, the meanings assumed by $R^1$ and $R^3$ being independent from one another, and the pharmaceutically acceptable salts thereof.

3. A benzo (b) thiophene of claim 1 wherein $X^1$, $X^3$, $X^8$ and $X^9$ are hydrogen.

4. A benzo (b) thiophene of claim 2 wherein $X^1$, $X^3$, $X^8$ and $X^9$ are hydrogen.

5. A benzo (b) thiophene of claim 3 wherein $R^1$ and $R^2$ are lower alkyl having up to 5 carbon atoms.

6. Hypocholesterolemiant and hypolipemiant pharmaceutical composition in unit dose, each unit dose comprising from 0.05 to 1.5 g of a benzo (b) thiophene of formula:

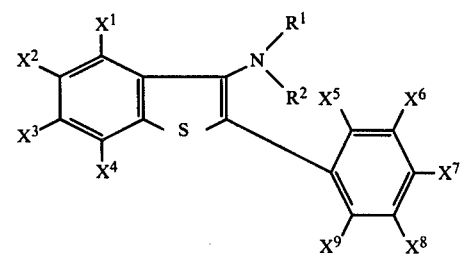

in which $X^1$ to $X^9$ which are identical or different are hydrogen, alkyl having up to 3 carbon atoms, chlorine, bromine, methoxy or methylthio, $R^1$ is hydrogen, alkyl having up to 8 carbon atoms, optionally chlorinated, brominated or methoxylated, phenyl optionally chlorinated or methoxylated, aralkyl having in all up to 9 carbon atoms optionally chlorinated or methoxylated on the phenyl nucleus, $R^2$ is hydrogen, phenyl, or a radical of formula:

in which A is two hydrogen atoms or one oxygen atom and $R^3$ can have the same meanings as given for $R^1$, $R^1$ and $R^2$ being not both hydrogen, the meanings assumed by $R^1$ and $R^3$ being independent from one another or the group

forms the radical piperidino, pyrrolidino, morpholino or piperazino which, in the case of piperazino, can, as appropriate, be substituted on the second nitrogen atom by an alkyl having up to 6 carbon atoms, by an aliphatic or aromatic acyl having up to 8 carbon atoms, by an optionally chlorinated or methoxylated phenyl or by an aralkyl optionally chlorinated or methoxylated on the phenyl nucleus, having in all up to 9 carbon atoms, and the pharmaceutically acceptable, salts thereof in admixture with a therapeutically acceptable vehicle.

7. Hypocholesterolemiant and hypolipemiant pharmaceutical composition in unit dose, each unit dose comprising from 0.05 to 1.5 g of a benzo (b) thiophene of formula:

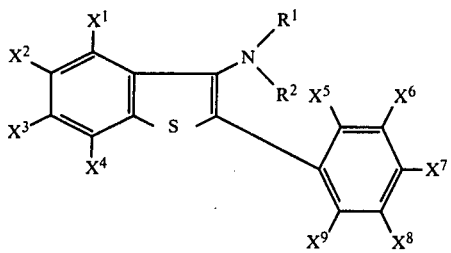

in which $X^1$ to $X^9$ which are identical or different are hydrogen, alkyl having up to 3 carbon atoms, chlorine, bromine, methoxy ormethylthio, $R^1$ is hydrogen, alkyl having up to 8 carbon atoms, optionally chlorinated, brominated or methoxylated, phenyl optionally chlorinated or methoxylated, aralkyl having in all up to 9 carbon atoms, optionally chlorinated or methoxylated on the phenyl nucleus, $R^2$ is hydrogen, phenyl, or a radical of formula:

in which A is two hydrogen atoms or one oxygen atom and $R^3$ can have the same meanings as given for $R^1$, the meanings assumed by $R^1$ and $R^3$ being independent from one another, and the pharmaceutically acceptable salts thereof, in admixture with a therapeutically acceptable vehicle.

* * * * *

UNITED STATES PATENT AND TRADEMARK OFFICE
CERTIFICATE OF CORRECTION

PATENT NO. : 4,157,399
DATED : June 5, 1979
INVENTOR(S) : Fritz SAUTER

It is certified that error appears in the above—identified patent and that said Letters Patent are hereby corrected as shown below:

[30] Foreign Application Priority Data

Dec. 23, 1976   [AT]  Austria   9587/76

Sep. 12, 1977   [AT]  Austria   6527/77

Sep. 12, 1977   [AT]  Austria   6528/77

Signed and Sealed this

Eleventh Day of December 1979

[SEAL]

Attest:

SIDNEY A. DIAMOND

Attesting Officer     Commissioner of Patents and Trademarks